(12) United States Patent  
Lopretti

(10) Patent No.: US 8,133,869 B2
(45) Date of Patent: Mar. 13, 2012

(54) COMPOSITIONS CONTAINING POLY[BETA(1,4)-2-AMINO-2-DEOXYGLUCOPYRANOSE] OLIGOMERS IN A SOLUTION OF MODIFIED LIGNIN PHENOLS AND THEIR USES

(75) Inventor: Mary Lopretti, Montevideo (UY)

(73) Assignee: Mary Lopretti, Montevideo (UY)

( * ) Notice: Subject to any disclaimer, the term of this patent is extended or adjusted under 35 U.S.C. 154(b) by 951 days.

(21) Appl. No.: 12/042,449

(22) Filed: Mar. 5, 2008

(65) Prior Publication Data

US 2008/0220974 A1    Sep. 11, 2008

(30) Foreign Application Priority Data

Mar. 7, 2007  (UY) .......................................... 30193

(51) Int. Cl.
| | |
|---|---|
| *A01N 25/00* | (2006.01) |
| *A01N 59/24* | (2006.01) |
| *A01N 25/02* | (2006.01) |
| *A01N 31/00* | (2006.01) |
| *A01N 43/04* | (2006.01) |
| *A61K 31/70* | (2006.01) |
| *A61K 31/08* | (2006.01) |

(52) U.S. Cl. ............ 514/22; 514/55; 514/731; 424/405; 504/189; 504/362; 504/354

(58) Field of Classification Search .......................... None
See application file for complete search history.

(56) References Cited

U.S. PATENT DOCUMENTS 4,397,841 A * 8/1983 Johnson ........................ 530/383
2004/0234662 A1* 11/2004 Ben-Yehoshua .............. 426/532

OTHER PUBLICATIONS

Reddy et al., J. Agric. Food Chem., 199, 47, 1208-1216.*
Tikhonov et al., Carbohydrate Polymers, 2006, 64, 66-72.*

* cited by examiner

*Primary Examiner* — Johann Richter
*Assistant Examiner* — Abigail Fisher
(74) *Attorney, Agent, or Firm* — Baker & Hostetler LLP

(57) ABSTRACT

The present invention refers to biocidal mixtures with disinfecting and microbicidal activity which also enhance root growth, containing as active ingredients poly[beta(1,4)-2-amino-2-deoxyglucopyranose] oligomers as per formula I, and oxidized natural lignin phenols with a low molecular weight. It also refers to agronomically efficient compositions against fungi, bacteria, insects and nematodes which are harmful to plants in agricultural crops, as well as their uses in agriculture.

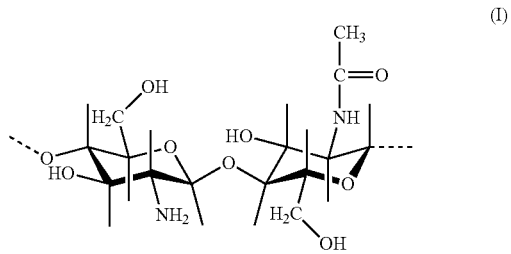

(I)

6 Claims, No Drawings

COMPOSITIONS CONTAINING POLY[BETA(1,4)-2-AMINO-2-DEOXYGLUCOPYRANOSE] OLIGOMERS IN A SOLUTION OF MODIFIED LIGNIN PHENOLS AND THEIR USES

CROSS-REFERENCE TO RELATED APPLICATIONS

This application claims priority to Uruguay Patent Application No. UY30193, filed on Mar. 7, 2007, which is incorporated by reference herein in its entirety.

TECHNICAL FIELD

The present invention refers to biocidal mixtures with disinfecting and microbicidal activity which also enhance root growth, containing the following active components:
1) poly[beta(1,4)-2-amino-2-deoxyglucopyranose] oligomers as per formula I,

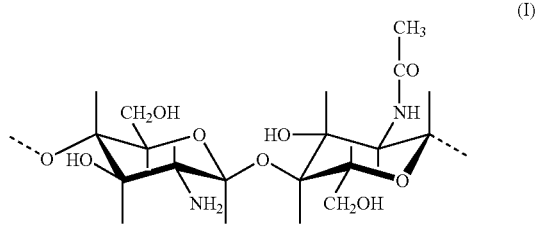

and
2) oxidized natural lignin phenols with a low molecular weight in synergically active and effective amounts.

BACKGROUND OF THE INVENTION

1. Chitin and Chitosan.

Poly[β(1,4)-2-amino-2-deoxyglucopyranose] oligomers are known in the art as chitosan and its preparation and action as a nematicide has been abundantly discussed in specialized literature. It is also known to produce stimulatory action on chitinolytic microorganisms.

The term "oligomer" herein refers to a polymer with a low molecular weight; specifically, a chitosan polymer.

As it is well known, poly[beta(1,4)-2-amino-2-deoxyglucopyranose], hereinafter referred to as "Chitosan", is produced by deacetylating the β(1,4)-2-acetamide-2-deoxy-D-glucose chitin, by hydrolysis thereof in an alkaline medium, usually NaOH or KOH, at high temperatures. This reaction and the resulting degree of deacetylation is sensitive to alkali concentration, particle size and solution density.

The term "deacetylation" as used herein refers to removal of one acetyl group ($-CO-CH_3$) from every chitin ring.

The term "degree of deacetylation" or "deacetylation %" as used herein refers to the percent ratio between amino groups/amido groups in the chitosan polymer. Some colorimetric methods such as the one described by Roberts & Domsey use the following ratio % $DA=(1-A_{1655}/A_{3340}\times 1/1.33)\times 1100$, where A is the logarithmic ratio of absorbance to transmittance at a given wavelength.

Natural chitin can be found mainly in the shells of crustaceans and in the exoskeletons of insects, as well as in cell walls of many fungi such as ascomycota, zygomycota, basidiomycota and deuteromycota, and yeasts, and seaweeds such as diatoms. [Muzzarelli R. in "Chitin". Pergamon Press. First Edition. 1974]. It is totally insoluble in water or in acid media. Additionally, native chitin is accompanied by inorganic salts, calcium carbonate being the most frequent among them, so it must be processed from its original matrix through successive deproteinization steps in an alkaline medium and demineralization in an acid medium.

Complete deacetylation of chitin results in a material that is totally soluble in an acid medium known as chitan. When deacetylation is incomplete, a mixture of chains is formed having different proportions of β(1,4)-2-acetamide-2-deoxy-D-glucose and β(1,4)-2-amino-2-deoxy-D-glucose units whose ratio depends on reaction conditions and therefore generate polymers with random molecular structures differing among them. [Lárez, Cristóbal. in "Algunos usos del Quitosano en sistemas acuosos". Revista Iberoamericana de Polímeros, Vol 4(2), 2003]. Said differences include their length, the percentage of amino acetyl groups present and their positions along the chain. Chitin deacetylation procedures are known and available to those skilled in the art.

It is particularly preferred to use chitin deacetylase, the enzyme that catalyzes conversion of chitin into chitosan by deacetylating the residues of N-acetyl-D-glucosamide. This enzyme was first identified and partially purified from extracts of the *Mucor ouxii* fungus. Nevertheless, its use could result in reduced efficiency to deacetylate insoluble chitin substrates. This problem has been overcome by previously treating the crystalline substrates of chitin to ease access of acetamide groups to the enzyme.

Solubility in water of salt polyelectrolytes of chitosan in an acid reaction depends on the nature of anions involved, the degree of deacetylation, the molecular weight of the polymer and temperature. If deacetylation of the original chitin does not produce a ratio of at least 60% amino groups to amido groups in the polymer, it will continue to be insoluble in water, even if it is soluble in an acid to neutral medium due to protonization of the amino groups, given that they have a pKa value of about 6.5. In other words, chitosan is a bioadhesive and easily bonds with negatively charged surfaces, such as membranes. Chitosan improves transportation of polar molecules through epithelial surfaces. Nonetheless, some procedures are known in the art allowing production of water soluble chitosans, in spite of degrees of deacetylation with an amino/amido ratio below 60%. In fact, the maximum degree of deacetylation has been found to be 75-85%.

The yield of chitosan production is assessed by reaction with ninhydrin, determining the blue-violet staining of complexes formed between the amino groups of chitosan and the ninhydrin added to test tubes containing 1 ml of chitosan solution at different concentrations, and boiled for 10 min. Quantification is made by comparison with a calibration curve previously set to relevant ranges. This technique is described in Bohinnski, "*Bioquímica*" 5th edition. Pearson, 1991; Van Hola, Mathew, "*Bioquímica*" 3rd ed, Pearson, 2004; and Feseden & Feseden, "*Química Orgánica*", Interamericana, 2002; and is well known in the art.

Additionally, Chitosan has the property of biodegradability making it an especially preferred polymer material [Muzzarelli R. in "*Chitin*". Pergamon Press. First Edition. 1974].

Chitosan oligomers offer many benefits over a large number of plant species, and there is abundant literature to support this fact. Usage of chitin and chitosan in agriculture is focused on improving the agronomical yields of several mechanisms. Seeds covered with chitosan solutions show improved sprouting and produce high yields when harvested. Horticultural products are frequently subject to mechanical damages, physiological alterations or attacks from pathogenic agents so using chitosan on these products results in a protective microbial activity and provides them with a cover generated by the filmogenic property of its solutions. These films are semipermeable to oxygen and carbon dioxide and also have proved to be antifungal, and therefore, they improve the quality and extend the useful life of treated fruits.

It has also been reported that an important benefit is the protection they provide on treated parts regarding attacks from bioantagonists such as bacteria, insects and nematodes.

Xiao Fei Liu et al in "*Antibacterial action of chitosan and carboxymethylated chitosan*" (Journal of Applied Polymer Science, vol. 79(7), 1324-1335, 2001) disclose the conclusions of applying chitosan with different molecular weights in order to assess the antibacterial action against *E. coli* in a lab culture containing meat extract, peptone and agar. The antibacterial action of chitosan is influenced by its molecular weight, the degree of deacetylation, its concentration in the solution and the pH of the medium. In particular, the test shows that water soluble chitosan produces a good antibacterial action against *E. coli* which increases with a molecular weight between 5000 and $9.16 \times 10^4$ Da, and decreases when molecular weight of the polymer increases to between $9.16 \times 10^4$ and $1.08 \times 10^6$ Da. Besides, the antibacterial activity of oligomers (polymers with a low molecular weight) has been proved to be caused mainly by inhibiting DNA transcription.

El Ghaouth, Ahmed et al, of Laval University, Quebec, Canada have published several scientific works showing the antifungal activity of chitosan. In "*Efecto de la Aplicación de Quitosano para controlar Botrytis en Pimentón*" (*Physiol. and Molec. Plant Pathology*, vol. 44, 417-432, 1994) they communicate the results of treating cuts in the peduncles of peppers with chitosan solution that were later infected with spores of *Botrytis cinerea*. It could be found that fruits treated with chitosan did not exhibit a visible disease until 7 days after inoculation, instead, in control fruits the disease was visible within 24 hours. A further review made 14 days later showed that all control fruits were infected, whereas only 25% of fruits treated with chitosan were infected.

In "*Efecto de la Aplicación de Quitosano in-vitro a hongos patógenos*" (Phytology Department, Laval University, Quebec, Canada) the antifungal effect of chitosan was researched through the growth (in-vitro) of common pathogenic fungi in postharvest strawberries. Research showed that chitosan substantially reduces the radial growth of *Botrytis cirenea* and *Rhizopus stonolifer* to great effect under high concentrations. These authors also confirmed the significance of the amount of positively charged groups ($-NH_3^+$) along the polymer chain.

In "*Efecto de la Aplicación de Quitosano para Controlar Pythium e inducir reacciones de defensa en Pepinos*" (*The American Phytopathological Society*, Vol. 84, 313-320, 1994) the authors grew a cucumber plant contaminated with *Pythium aphanidermatum* in a solution with nutrients to which chitosan was added. As a result, root putrefaction could be controlled and a number of defensive responses were activated, including induction of structural barriers in root tissues and stimulation of antifungal enzymes in both roots and leaves, without causing any residual toxic effects in the plants.

Benhamou, Nicole and Theriault, George in "*Efecto de la Aplicación de Quitosano para el control de Fusarium en Tomate*" (*Physiol. and Molec. Plant Pathology*, 33-52, 1992) disclosed the results of applying chitosan to tomato plants before inoculation with the root pathogen *Fosarium oxysporum* f. sp. *Radicis-lycopersici*. Research showed that chitosan effectively protected the plant against putrefaction of the neck and root. It also showed that it is not only useful in stimulating the general defense system of plants but also in reducing the effect of prevalent pathogens in the soil such as *Fusarium*. Protection against fungal attack on the roots could be observed for more than 6 days.

Concerning the present invention, the nematicide activity property of these polymers is preferred. It has been shown that said nematicide activity is effective in species such as vegetables, asparagus, pulses, cereals, oilseeds, beetroot, cotton, tobacco, fruit plants, ornamental plants, woods, tomatoes and peppers. The mechanism of protection with nematicide activity is attained by inducting a physical barrier in seeds as well as in plant roots, even though there also exist other mechanisms such as activating resistance genes, activating proteins connected with resistance responses, or activating chitinase or accumulation of physaline, an antibiotic and antifungal, or a combination thereof.

Carrera, L. et al in "*Efecto Nematicida de Enmiendas de Quitina y Quitosano sobre el Nematodo Nodulador*" (Polymer Lab, National University, Costa Rica) discloses performance of replicated tests ($\times 6$) in soils affected by nematodes of the *Meloedogyne* sp. type in experimental tomato crops (*Lycopersicon esculentum* MILL, Hayslip variety) in pots, with three weeks of vegetative growth, applying doses of 0, 0.2, 0.4, 0.8, 1.0 w/w of chitin and chitosan. Some significant parameters of nematicide activity were assessed, such as plant height, fresh weight of roots, number of galls in roots, gall index, number of nematode infective stages (J2) in 100 g of soil, number of nematode eggs in 25 g of root, and pH. In the conclusions they reported that the number of infective stages of *Meloedogyne* sp. and the number of eggs by root weight as related to increasing doses of chitin were highly significant. 0.8% and 1% doses of chitin were very effective and comparable to conventional chemical treatment, whereas chitosan in a dose of 0.8% showed a clear tendency to control the microorganism.

Particularly relevant and setting an important precedent was the experimental assay developed in order to comply with the requirements for registration of the BIOROOT (NEMATICID)® product, owned by the inventors of the present invention, before the Ministry of Cattle, Agriculture and Fisheries of Uruguay. In said experimental work, they performed a "*comparative research of poly[beta(1,4)-2-amino-2-deoxyglucopyranose] as a stimulant for root growth and as a protective agent from nematode colony growth*" (Lopretti, Mary et al, 2006) in greenhouse tomato crops (*Lycopersicom esculentum*) of the hybrid NIXE variety and hybrid pepper (*Capsicum anum*), autumn-winter cycle, and assessing the results using statistical techniques known to those skilled in the art. A 2% chitosan solution produced from chitin was used, in order to verify the root growth action together with the protective and nematostatic action. This work concluded that a stimulating effect of root growth showed in plants treated with chitosan, wherein an increase in root width and mostly in root length could be confirmed. This increase allows for improved anchoring, improved exploration ability and improved water and nutrient absorption, which is made apparent by larger leaf areas, with larger fruits than control plants. Furthermore, it was concluded that using these natural polymers, both chitin and chitosan, formation of chitinolytic agents is enhanced.

In brief, and taking into account the scope of the present invention, usage of chitosan, a natural, biodegradable and non-toxic polymer of a cationic type, protects treated parts of soils, plants and parts of plants, such as roots, stems, leaves, seeds, flowers and fruits, more preferably roots, from the attack of bioantagonists such as bacteria, fungi, insects and nematodes. This provides the plant with greater tolerance to neck and root health problems increasing the vitality of plant cells, accelerating degradation of cell walls in fungi and organisms containing chitin in their structure, delivering additional chitosan in the process. In addition to this, it stimulates plant cells to produce biochemical compounds that strengthen cell walls, thus significantly improving resistance to stress situations, drought, excessive dampness, transplants and frost. An increase in root mass is triggered, which translates into an increase in the speed of growth and greater plant vigor.

2. Lignin

Lignin is an aromatic, non carbohydrate complex, of which many structural polymers exist. It is a macromolecule, with a high molecular weight resulting from the union of phenylpropyl alcohols: cumaryl, coniferyl and sinapyl whose structures are as follows:

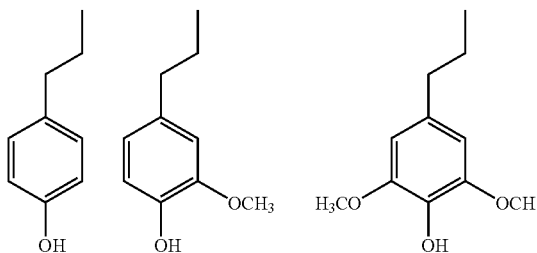

Randomized coupling of these molecules produces a three-dimensional, polymeric and amorphous structure, depending on the source of raw material for lignin production. This is why it is not possible to describe a definite structure, although there is a plurality of models providing approximate representations of said structure, one of which is illustrated below by way of example:

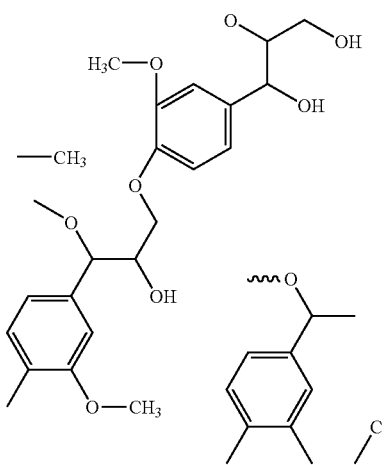

However, for the purposes of the present invention, this fact is not relevant. They are insoluble in acids and soluble in strong alkalis, such as NaOH.

Lignin is the main constituent of secondary wall cells in plant fibers, providing rigidity for structural support, and impermeability for water transport. After cellulose, this polymer is the most abundant organic compound in the biosphere. In different species of trees, lignin contents vary between 15 and 36% of dry wood material.

Processes to produce modified lignin phenols have been described and are known in the art.

Particularly, patent application UY26.985 (Uruguay) filed on Oct. 25, 2001, by the same inventor of the present invention, and incorporated by reference herein in its entirety, discloses a method to produce it using biotechnological means based on the fact that some microorganisms, such as fungi, bacteria, etc. are able to modify lignin. For the scope of the present invention, it is preferred that such microorganisms be fungi, including the following genera: *Coriolus* spp, *Phanerochaetes* spp, or *Gloeophylum* spp, in whose enzymatic extracts the following enzymes can be found: Lig-peroxidase, Mn-peroxidase, Poliblue-oxidase, demethylases, and oxygenases, among others. Particularly preferred are so-called brown rot fungi, such as *Gloeophyllum trabeum*, and so-called white rot fungi, such as *Phanerochaete chrysosporium*. Both types of fungi demethoxylate lignin producing hidroxyl groups in phenolic or non-phenolic structures, and produce oxidation of lateral chains and cleavages in aromatic rings. Brown rot fungi produce their main effect by demethoxylating aryl methoxyls, thus increasing the number of phenols. White rot fungi are characterized by depolymerizing lignin with a Lig-peroxidase or Mn-peroxidase, and they are the only known organisms able to degrade it completely into carbon dioxide and water.

In the present invention, it is preferred that this component of the biocidal composition be a mixture of oxidized natural phenols with a low molecular weight.

The production process described in UY26.985 includes the following steps: characterizing lignin, preparing the enzymatic biological agent by culturing fungi or obtaining enzymatic extracts from these fungi; depolymerizing lignin in a biological fermenter under controlled conditions; separating the phases, where the solid phase is obtained by precipitating lignins with a high molecular weight; filtering; extracting soluble modified phenols with centrifugation; purifying modified phenols with precipitation; characterizing and controlling the quality of the final product of the mixture of modified phenols whose molecular weight is less than 800; and controlling bactericide and fungicide activity.

In this method, the phenol hydroxide contents were analyzed according to the method described by Goldschmid, well known in the art, where a reference calibration curve of lignin is used vs. absorbance at 280 nm on samples obtained 0 hours after enzymatic fermentation and up to 192 hours after it began. Biomass changes during fermentation were analyzed by determining the weight/volume ratio of fermentation media 0 hours and 144 hours after fermentation began.

The term "natural phenols" as used herein refers to phenols from a plant source obtained with the strategy of enzymatic biotechnological production disclosed in UY26.985, where demethoxylation of phenols occurred exclusively by the oxidizing action of the enzymes of fungi and bacteria. The term "natural phenols" is used as opposed to other phenols that are produced by organic synthesis in labs or derived from oil.

For the purposes of the present invention, it is a relevant fact that phenols used in the biocidal composition of the invention that will be described below should be natural using the enzymatic processes of fungi and bacteria which can be found in the vicinity of the plant to be protected and in surrounding soil.

The term "modified phenols" as used herein refers to phenols oxidized by the above mentioned enzymatic processes.

The term "demethoxylation" as used herein refers to removal of one or two methoxide groups (—O—$CH_3$) linked to the phenol ring, substituting it for a —H.

Under the conditions described in the paragraphs above, a final product is obtained, which is biocidal, enhancing plant resistance to phytopathogenic agents and which is based on modified natural phenols from plant sources that provide protective activity against said phytopathogenic agents, and which are particularly and preferably interesting for the composition of the present invention.

3. State of the Art

In concordance with the description under "Background of the Invention", the state of the art shows that chitosan, with its disclosed properties and marketed products containing it, provides an excellent ability to control bacteria, insects and nematodes, especially nematodes, by increasing chitinolytic flora, but concomitantly it shows an inefficient fungicide activity.

On the other hand, Lignin shows an efficient fungicide action against phytopathogens such as *Botritis, Esclerotinia*, etc. and facilitates transformation of organic materials in soils, but has no fungicide action on fungi affecting lignin and has a very inefficient bactericide activity.

No composition for agricultural use has been disclosed meeting the requirements to obtain in a single composition the synergy of a disinfecting action against soil fungi and bacteria together with bacteriostatic and fungistatic activity and bactericide, fungicide, microbicide and nematicide activity, all of them provided in agronomically efficient doses.

SUMMARY OF THE INVENTION

The inventors of the present invention have found that a composition containing a mixture of the following active components 1) poly[beta(1,4)-2-amino-2-deoxyglucopyranose] oligomers as per formula I,

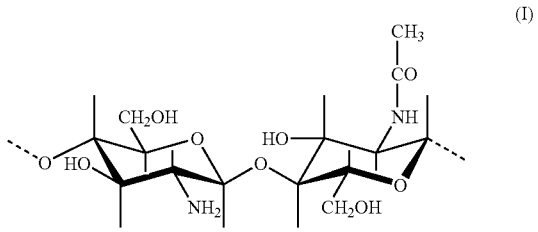

(I)

and 2) oxidized natural lignin phenols with a low molecular weight at certain concentrations, provides an activity with the desired characteristics and the synergy found in the components provides an efficient composition for agricultural use with new characteristics.

The mixture of a molecule of chitosan oligomers in a soluble form added to a phenol from a plant source, which is generally used for its germicide action, acquires a synergy that provides a protective action by forming a film on the plant or the soils which are the purpose of this invention, which, together with the biocidal effect of added phenol also provides a microbicidal effect depending on the dose.

Agricultural use of this composition provides protection to the roots and stimulates root growth acting as a physiological regulator. The root protection action is obtained by forming a thin film allowing for the exchange of gases, nutrients and water through it, but protecting the root from attacks by pathogenic agents in the soil, particularly nematodes.

Therefore, the aim set for the present invention is to design a composition with a disinfecting action against soil fungi and bacteria, with bacteriostatic and fungistatic activity and bactericide, fungicide, microbicide and nematicide activity, all of them provided in agronomically efficient doses, which could satisfy agricultural market demand and produce better results in the fight against harmful fungi, bacteria, insects and nematodes, while simultaneously optimizing the total number of active agents applied to the soil and to the plants.

According to this, the mixtures defined at the beginning of this document were found, which hereinafter shall be called "phenol-poly(N-acetylglucosamine) complex". It was also found that if compound (1) and compound (2) were simultaneously applied, action against harmful fungi and nematodes was better than if each one was applied on its own.

The new composition, phenol-poly(N-acetylglucosamine) complex of the present invention is especially important in combating fungi, bacteria, insects and nematodes affecting several crop plants such as vegetables, asparagus, pulses, cereals, oilseeds, beetroot, cotton, tobacco, fruit plants, ornamental plants, woods, tomatoes and peppers, more specifically lettuces, tomatoes and peppers. Said composition is particularly useful in combating the following phytopathogenic fungi, as shown in previous tests. Whereas other soil fungi such as *Pleurotas, Trichoderma harzianum, Aspergillus* sp, *Penicillinim* sp, among others, are diminished but still remain. A preferred embodiment of the present invention involves that phenols used in the biocidal composition of the invention should be natural using the enzymatic processes of fungi and bacteria found in the surroundings of the plant to be protected, which is one of the significant new aspects of the present invention.

The present invention also provides a mixture with synergic activity such that when both active components are mixed in an aqueous solution, the nematicide component (1) microencapsulates units of phenol polymers of component (2) with a film thereof thus providing the mixture solution with the property of extending the availability of component (2) over time, at least twice the amount of available time than when it is applied alone and separately. The fungicide component (2) in turn provides sanitary stability to the oligomer solution (component (1)) due to its own biocidal property.

By virtue of the ionic properties of oligomers in the phenol-poly(N-acetylglucosamine) complex of the present invention, the aqueous solutions thereof should be stabilized to a pH range for which chemical action is efficient. Said pH must be within the pH range of 4-7, more preferably, 5-7, and even more preferably, 5.5-7. In order to achieve required acidity, the acidulating agent must be a weak acid, which could be inorganic or organic, selected from the group consisting of: phosphoric acid, acetic acid, sulphinic acid, lactic acid, citric acid. Use of acetic acid is particularly preferred.

Mixtures according to the invention, or otherwise made up of components (1) and (2) can be prepared in usable formulations, for example in solid immobile forms, such as powders, fine grains and granulated, or in an aqueous liquid phase, as in microencapsulated solutions or emulsions as explained above.

Typically, mixtures of the compounds of the invention are used in aqueous solutions, which ensures a uniform and homogenous distribution in the soil, the plant, its parts, at a locus in the plant or in seeds; therefore mixtures of components (1) and (2) in an aqueous medium with an acidulating agent to regulate solution pH selected from the above mentioned group are especially preferred.

Solutions are prepared using methods known in the art.

Required purity for components (1) and (2) of the composition of the invention does not require exceeding agronomical purity levels.

As used herein, the term "agronomical purity" means a concentration of 99% of the desired product, admitting presence of non-toxic chemical contaminants coming from the original chitin or lignin matrix, and the reagents used in the production methods of chitosan oligomers and modified lignin phenols. The presence of salts is generally admitted, such as nitrates, sulphates, sodium chloride, calcium, magnesium, which are also useful for metabolism of the soil.

Agronomically efficient doses of the mixture of components (1) and (2) to create the phenol-poly(N-acetylglucosamine) complex according to the invention, shall depend mainly on the initial degree of infection, the physical and chemical characteristics of the soil, the type of culture, and the climatic condition (seasonality). Tested doses include chitosan oligomers with a molecular weight equal to or less than 10.000 g/mol, between 1% and 10% (by volume), and modified lignin phenols with a molecular weight equal to or less than 800 g/mol, between 2% and 10% (by volume). Any combination of the components containing percentages included between these ranges, including 10:10 (by %) (v/v) or 1:2 (by %) (v/v) of chitosan:modified phenols, have proved to be agronomically efficient.

However, in the present invention the preferred ratio of chitosan:modified phenols is 9:7 (by %) (v/v); more preferably 9:5 (by %) (v/v); even more preferably 8:3 (by %) (v/v) and yet more preferably 8:2 (by %) (v/v).

Concentrations of any of them above 10% will act on the soil with a toxicity degree that will produce moderate to total mortality of microorganism species in the metabolic cycle of soils. Concentration levels of active ingredients of the invention herein disclosed are levels compliant with biological and agronomical safety.

The timing of application of the phenol-poly(N-acetylglucosamine) complex of the invention shall depend on agricultural practices, on the specific crop and on its sanitary conditions. However, the phenol-poly(N-acetylglucosamine) complex of the invention is applicable at any time during cultivation: preparing the soil, transplanting hotbeds, producing layers, implanting layers, development stages, harvesting, and it is not subject to any protocols other than the recommendations of experts in the agronomic and agricultural art. The actions and properties of the phenol-poly(N-acetylglucosamine) complex of the present invention can be shown through the following assays.

DETAILED DESCRIPTION OF THE INVENTION

Examples

The following examples are included to demonstrate preferred embodiments of the invention. It should be appreciated by those of skill in the art that the techniques disclosed in the examples which follow represent techniques discovered by the inventor to function well in the practice of the invention, and thus can be considered to constitute preferred modes for its practice. However, those of skill in the art should, in light of the present disclosure, appreciate that many changes can be made in the specific embodiments which are disclosed and still obtain a like or similar result without departing from the spirit and scope of the invention.

Example 1

Application example 1—Check the action of the phenol-poly(N-acetylglucosamine) complex on culture media inoculated with a mixture of *Pleurotas, E. coli, Trichoderma harzianum, Aspergillus* sp, *Penicillinim* sp.

Three working solutions were prepared:
"solution (A)": solution of chitosan 5% (w/v)
"solution (B)": solution of lignin 10% (w/v)
"solution (C)": solution (A) and solution (B) in a 1:1 weighted ratio.

Additionally a cocktail was prepared containing fungi and bacteria typical of the soil of these crops, including: *Trichoderma harzianum+Aspergillus* sp.+*Penicillium* sp., and *E. coli*. was used as bacterial control.

Method:
a) In PCA plates (plate agar count) 1 ml of the above mentioned solutions was sown on the surface under non aseptic conditions in duplicate. This was left at room temperature for 7 days, controls being performed after 24, 48, 72 and 144 hours.
b) Filter paper discs were impregnated with the above solutions for 3 hours under non aseptic conditions, they were dried in a drying oven. Then, discs were placed on the center of plates containing different growth media. Plates were sown with fungi which grow in lignocellulosic plants such as the *Pleurotus* genus and also with bacteria such as *E. coli*. Both were incubated under aerobic conditions at 25° C. as per diagram I. Plates with non impregnated discs were used as control. Invasion of the disc was recorded every 24 hours.

Diagram I. Working Diagram for Invasion Analysis.

| MEDIUM | PLATE N° | BACTERIUM OR FUNGUS | INCUBATION CONDITIONS | DISC IMPREGNATED WITH |
|---|---|---|---|---|
| PDA | 1 | *Pleurotus* | Aerobic 25° C. | Lignin |
| PDA | 2 | *Pleurotus* | Aerobic 25° C. | Chitin |
| PDA | 3 | *Pleurotus* | Aerobic 25° C. | Non impregnated control |
| PCA | 4 | *E. coli* | Aerobic 25° C. | Lignin |
| PCA | 5 | *E. coli* | Aerobic 25° C. | Chitin |
| PCA | 6 | *E. coli* | Aerobic 25° C. | Non impregnated control | c) Filter paper discs previously sterilized in autoclave were impregnated with solutions A and B under aseptic conditions. Discs were placed at the center of the PDA plates. The plates were sown with a fungi cocktail containing *Trichoderma harzianum, Aspergillus* sp. and *Penicillium* sp. and they were incubated as per the following diagram (II).

Diagram II. Working Diagram for Invasion Analysis with a Fungi Cocktail.

| MEDIUM | PLATE N° | COCKTAIL FUNGUS | INCUBATION CONDITIONS | DISC IMPREGNATED WITH |
|---|---|---|---|---|
| PDA | 1 | *Trichoderma harzianum, Aspergillus*, sp. *Penicillium* sp. | Aerobic drying oven 25° C. | Chitin |
| PDA | 2 | *Trichoderma harzianum, Aspergillus* sp., *Penicillium* sp. | Aerobic drying oven 25° C. | Lignin |

-continued

| MEDIUM | PLATE N° | COCKTAIL FUNGUS | INCUBATION CONDITIONS | DISC IMPREGNATED WITH |
|---|---|---|---|---|
| PDA | 3 | *Trichoderma harzianum*, *Aspergillus*, sp. *Penicillium* sp. | Aerobic drying oven 25° C. | Non impregnated control | d) Work was done with a mixed system using some soil fungi and *E. coli* for bacterial control. The method was the same as for assays with fungi and bacteria performed separately. A temperature of 25° C. was kept because that is the average room temperature.

Diagram III. Working Diagram for Invasion Analysis with a Fungi and Bacteria Cocktail.

| MEDIUM | PLATE N° | COCKTAIL FUNGI AND BACTERIA | INCUBATION CONDITIONS | DISC IMPREGNATED WITH |
|---|---|---|---|---|
| PDA | 1 | *Trichoderma harzianum*, *Aspergillus*, sp. *Penicillium* sp. *E. coli* | Aerobic drying oven 25° C. | Chitin |
| PDA | 2 | *Trichoderma harzianum*, *Aspergillus* sp., *Penicillium* sp. *E. coli* | Aerobic drying oven 25° C. | Lignin |
| PDA | 3 | *Trichoderma harzianum*, *Aspergillus*, sp. *Penicillium* sp. *E. coli* | Aerobic drying oven 25° C. | Lignin * Chitin 1:1 |

Results in connection with the Biocidal effect:

TABLE 1

Results obtained up to 6 days after sowing

| Solution | 24 hs | 48 hs | 72 hs | 144 hs (6 days) |
|---|---|---|---|---|
| Sol. A1 Chitin | — | — | A colony grew outside the area where solution A is located, and two colonies grew on the edge of the solution. Both seem bacterial. | The solution A area started to be invaded with three types of colonies: i) white, shining ii) white, dark (pyramid) (3 colonies) iii) white, dark (many) |
| Sol. A2 Chitin | — | — | 7 white colonies grew on solution A with the same morphology as in plate A1. | 2 types of colonies grew, a larger growth found where there is no solution |
| Sol. B1 Lignin | — | — | Bacterial growth becomes evident until it reaches the solution, it stops there (Image III) | Growth increases, still not invading the area with the solution |
| Sol. B2 Lignin | — | — | No evidence of growth | No evidence of growth |
| Sol. (A + B) | — | — | No evidence of growth | Few point-like colonies throughout the plate, much larger where there is no solution. |

Plates were controlled for another 13 days, growths continued following the same patterns, colony size increased and no cell death areas were found where the growth came into contact with the solution.

TABLE 2

Results from the invasion analysis of impregnated discs

| Medium | Disc | Bacterium/Fungus | Result |
|---|---|---|---|
| PDA | Lignin | *Pleurotus* | The fungus sown does not reach the disc area. Fungus grows in about a quarter of the disc area which is supposed to come from environmental contamination. |
| PDA | Chitin | *Pleurotus* | There is no invasion of the disc within 60 hours nor any growth that could come from environmental contamination. |
| PDA | Non impregnated control | *Pleurotus* | The fungus did not reach the disc area., there is growth coming from environmental contamination. |
| PCA | Lignin | *E. coli* | There is bacterial growth around the disc but it is unable to invade. There is fungus growth on the disc. |
| PCA | Chitin | *E. coli* | Bacterial growth around the disc but unable to invade. There is fungus growth on the disc. |
| PCA | Non impregnated control | *E. coli* | Growth throughout the plate with total invasion of the disc. |

TABLE 3

Results of the invasion analysis of sterile discs impregnated under aseptic conditions

| MEDIUM | COCKTAIL FUNGUS | DISC IMPREGNATED WITH | RESULT 48 HS | RESULT 144 HS |
|---|---|---|---|---|
| PDA | *Trichoderma Harzianum, Aspergillus, Penicillium* | Chitin | None totally reach the disc area. *Aspergillus* (25%) which starts reaching and seems to grow around the disc. *Penicillum* growth 10% plate. *Trichoderma* growth 3%. | *Aspergillus* (75% plate) invades the disc. *Penicillum* (25% plate) reaches the disc area but does not invade. *Trichoderma* (10% plate) does not reach the disc area, it seems its growth is restrained by *Aspergillus*. |
| PDA | *Trichoderma Harzianum, Aspergillus, Penicillium* | Lignin | *Penicillum* (20%) and *Trichoderma* (8%) do not reach the disc area. *Aspergillus* (50%) reaches and invades. | *Aspergillus* (100%) totally invades the disc. *Trichoderma* (10%) and *Penicillum* (20%), their growth seems restrained by *Aspergillus*. |
| PDA | *Trichoderma Harzianum, Aspergillus, Penicillium* | Non impregnated control | *Aspergillus* seems to start invading, this is the fungus that grew most (50% plate) *Trichoderma Harzianum* (3%) and *Penicillium* (10%) do not reach the disc area. | Invasion of the disc by *Aspergillus*, the other two growths are restrained and do not reach the disc area. |

TABLE 4

Results of the invasion analysis of sterile discs impregnated simultaneously with fungi and bacteria under aseptic conditions.

| MEDIUM | COCKTAIL FUNGI AND BACTERIA | DISC IMPREGNATED WITH | RESULT 48 HS | RESULT 144 HS |
|---|---|---|---|---|
| PDA | *Trichoderma Harzianum, Aspergillus, Penicillium E. coli* | Chitin | None reach the disc area. *Aspergillus* (45%) starts reaching and seems to grow around the disc. *Penicillum* growth 10% plate. *Trichoderma* growth 10%. *E. coli* grows to 5% of the plate very far from the disc | *Aspergillus* (85% plate) invades the disc. *Penicillum* (45% plate) reaches the disc area invading the edge. *Trichoderma* (40%) plate even invades the disc *E. coli* there is growth in plate 20% not reaching the edge of the disc |

TABLE 4-continued

Results of the invasion analysis of sterile discs impregnated
simultaneously with fungi and bacteria under aseptic conditions.

| MEDIUM | COCKTAIL FUNGI AND BACTERIA | DISC IMPREGNATED WITH | RESULT 48 HS | RESULT 144 HS |
|---|---|---|---|---|
| PDA | Trichoderma Harzianum, Aspergillus, Penicillium E. coli | Lignin | Penicillum (10%) and Trichoderma (4%) do not reach the disc area. Aspergillus (30%) reaches and invades. (Image VII b) E. coli appears point-like throughout the plate without reaching the control disc | Aspergillus (80%) totally invades the disc. Trichoderma 10% and Penicillum (20%), both seem to have their growth restrained by Aspergillus. E. coli appears point-like throughout the plate including the disc. |
| PDA | Trichoderma Harzianum, Aspergillus, Penicillium E. coli | Lignin * Chitin 1:1 | Aspergillus seems to start invading, this is the fungus that grew most (5% plate) Trichoderma harzianum (2%) and Penicillium (5%) do not reach the disc area. E. coli grows to 2% of the plate not reaching the disc. | Aspergillus; Trichoderma harzianum and Penicillium are restrained, not reaching the disc area. Percentages are maintained. E. coli grows to 5% of the plate without reaching the disc |

Example 2

Application example 2—Check the microencapsulating property of modified phenols in chitosan oligomers (phenol-poly(N-acetylglucosamine) complex) applied to greenhouse pepper crops of Elisa hybrid and Raza hybrid types, autumn-winter cycle.

[Assays Carried Out by Uruguayan Agricultural Authorities. Head Office of Agricultural Services—Ministry of Cattle, Agriculture and Fisheries]

Sanitary product: A primary solution was prepared containing 2% modified phenols and 1% chitosan. Under these concentrations, the amount of chitosan is optimal to microencapsulate the modified phenols and benefit the action of both components.

Formulation type: Liquid soluble concentrate.

Means of Action: Fungal controller with an extensive period of action.

Desired protection: against *Brotitis* and *Sclerotinia* (typical fungi in autumn-winter)

CHART 1

Summary of assay parameters, method of analysis and results attained.

| | Assay parameter | |
|---|---|---|
| | Assay 1 | Assay 2 |
| CROP PLOT | | |
| Sowing density | 3756 plants. One row of plants per bed with a distance between plants of 23 cm. | 2112 plants. One row of plants per bed with a distance between plants of 25 cm. |
| Plot description | 12 rows 72 m long; 1500 m$^2$ | 72 m long; 1000 m$^2$ |
| Watering system | Dripping | Knapsack sprayer |
| Soil type | Heavy clayey | Loamy sand |
| Previous crop | Melon | Tomato |
| Crop rotation in the plot | Tomato, melon, pepper | Tomato, melon, pepper |
| APPLICATION OF THE SANITARY PRODUCT | | |
| Dose | 300 ml in 100 L of water | 300 ml in 100 L of water |
| No. of applications | 5 | 2 |
| Water carrier expense per application | 50 L | 10 L |
| ANALYTICAL PARAMETERS | | |
| Analysis method | Absorbance at 280 nm | Absorbance at 280 nm |
| Analytical standard | Modified phenols | Modified phenols |
| ASSESSMENT OF THE ASSAY | | |
| Visual observation | New leaves sprout, normal flowering and fruit formation. | New leaves sprout, normal flowering and fruit formation. |
| Sanitary condition | Brotitis: 0 (not observed) Sclerotinia: 0 (no presence) | Brotitis: 0 (not observed) Sclerotinia: 0 (no presence) |
| Time span of controls | 24, 48, 72, 144, 288, 576 and 720 hs after application. | 24, 48, 72, 144, 288, 576 and 720 hs after application. |

Example III

Application example 3—Verification of the synergic effect of the phenol-poly(N-acetylglucosamine) complex as an enhancer of root growth.

Field crops already underway were provided with the solution immediately after transplant.

The crop soil had an average level of nematode infestation (Melodogyne). A soil was chosen with intensive, continued and non rotating usage, low on organic materials.

Plot description: the total area of the greenhouse was 1.000 m².

Schedule of crop installation:
Sowing date—Nov. 6, 2006
Transplant date—Dec. 4, 2007

Applied dose: 300 cc of chitosan solution and 300 cc of phenols solution by watering by dripping every 1.000 m². In 2500 liters of water per hour for every 1000 m².

Time span of application of the solution: once a week. Applied throughout January and February 2007.

The blank test was made with chitosan solution in the same proportion and applied with the same means.

Assay Follow-Up

The crop was installed and general observations were made, looking into its development over time. Crop health, flowering, plant color and fruit formation were observed, and also measurements were made ten weeks after transplant about the length and width of plant roots. The negative or positive presence of root nodules was also observed.

TABLE 5

Results on the presence of nodules, root length and width.

| Randomly picked plants | pathology | Root size | |
|---|---|---|---|
| Sample N° Plants | Nodule presence | Length (cm) | Width (cm) |
| 1 CQ | Negative | 14 | 16 |
| 2 CQ | Negative | 13 | 15 |
| 3 CQ | Negative | 15 | 16 |
| 4 CQ | Negative | 18 | 18 |
| 5 CQ | Negative | 15 | 18 |
| | | average 15 | average 16.5 |
| 1 TQL | Negative | 26 | 20 |
| 2 TQL | Negative | 18 | 18 |
| 3 TQL | Negative | 25 | 20 |
| 4 TQL | Negative | 24 | 22 |
| 5 TQL | Negative | 21 | 25 |
| | | Average 22.8 | Average 21 |

CQ (treated with chitosan solution)
TQ-L (phenol-chitosan complex)

Percentage improvement on root length: over 60%
Percentage improvement on root width: over 70%

Crop Assessment

No nodules were found at root level, and periodical applications stimulated root development in plants. When applications jointly include chitosan and phenol solutions in the form of phenol-poly(N-acetylglucosamine) complex of the invention, an increase in plant health and root development can be observed, resulting in an increase in the whole plant. Plant roots were larger, especially lengthwise, achieving improved anchoring, a greater exploration ability and a greater water and nutrient absorption ability.

Judging by the assay results it can be concluded that the phenol-poly(N-acetylglucosamine) complex of the invention is efficient as compared to the use and application of each of its components separately, where component (1) acts typically and specifically as a nematicide, and component (2) acts typically and specifically as a fungicide. Additionally, film microencapsulation generated by chitosan oligomers on the modified lignin phenols provide the composition with an antifungal action that lasts longer on the plant than independent application of modified phenols. Particular attention should be paid to the results under Example III which clearly show the effect on root growth of plants treated with the phenol-poly(N-acetylglucosamine) complex of the invention as compared to plants treated only with a chitosan solution. The synergy of the complex mixture has produced an improvement in root length of over 60% and in root width of over 70%.

Novelty of the Invention and Non-Obviousness

In brief, the new synergy provided by the present invention can be expressed as follows: the nematicide action provided by chitosan oligomers is improved and enhanced, because beneficial microorganisms present in soil persist, whereas any other agents (pathogenic or not, either bacteria or fungi) are diminished or eliminated, and therefore do not compete with the crop for nutrients in the surrounding soil. Besides, fungicide action of modified phenols produced via enzymatic means is improved and extended, because chitosan oligomers generate a protective film on them, such that if only modified phenol solutions were delivered to the soil of the crop the improvement would not exist.

As it has been found by the inventors of the present invention, this synergy is not obvious and has not been described in the state of the art as of the date of submission of this document.

What is claimed is:

1. A biocidal aqueous composition comprising a synergistic combination of:
   (1) an effective amount of a poly[beta(1,4)-2-amino-2-deoxyglucopyranose] oligomers as per formula I,

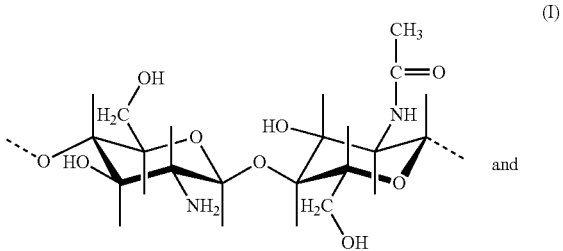

(2) an effective amount of an oxidized natural lignin phenols;
   (3) a weak acid; and
   (4) water, wherein the component (1) has a molecular weight equal to or less than 10,000 g/mol and it is between 1% and 10% (by volume), the component (2) has a molecular weight equal to or less than 800 g/mol and is present in the composition at between 2% and 10% (by volume).

2. The composition of claim 1, wherein component (1) and component (2) are in a 10:10 ratio by volume percentage (% v/v).

3. The composition of claim 1, wherein component (1) and component (2) are in a ratio selected from the group consisting of a 9:7 ratio (% v/v); a 9:5 ratio (% v/v); a 8:3 ratio (% v/v), and a 8:2 ratio (% v/v).

4. The composition of claim 1, wherein the weak acid is selected from the group consisting of phosphoric acid, acetic acid, sulphinic acid, lactic acid, and citric acid.

5. The composition of claims 1 wherein the pH is adjusted by the weak acidulating agent within a range selected from the group consisting of between 4 and 7, between 5 and 7, and between 5.5 and 7.

6. A method of protecting agricultural crop plants from fungi, bacteria, insects and nematodes, comprising the step of providing the composition of claim 1 to the plants.

* * * * *